US010426432B2

United States Patent
Shao et al.

(10) Patent No.: US 10,426,432 B2
(45) Date of Patent: *Oct. 1, 2019

(54) METHOD AND DEVICE FOR DETECTING ELASTICITY OF VISCOUS ELASTIC MEDIUM

(71) Applicants: Wuxi Hisky Medical Technologies Co., Ltd., Wuxi (CN); BEIJING SONICEXPERT MEDICAL TECHNOLOGY CO., LTD., Beijing (CN)

(72) Inventors: Jinhua Shao, Beijing (CN); Jin Sun, Beijing (CN); Houli Duan, Beijing (CN)

(73) Assignee: WUXI HISKY MEDIAL TECHNOLOGIES CO., LTD., Wuxi (CN)

(*) Notice: Subject to any disclaimer, the term of this patent is extended or adjusted under 35 U.S.C. 154(b) by 467 days.

This patent is subject to a terminal disclaimer.

(21) Appl. No.: 15/279,936

(22) Filed: Sep. 29, 2016

(65) Prior Publication Data

US 2017/0014103 A1    Jan. 19, 2017

Related U.S. Application Data

(63) Continuation of application No. 13/497,648, filed as application No. PCT/CN2010/077757 on Oct. 14, 2010, now Pat. No. 9,554,771.

(30) Foreign Application Priority Data

Oct. 15, 2009 (CN) .......................... 2009 1 0235731

(51) Int. Cl.
*A61B 8/00* (2006.01)
*A61B 5/00* (2006.01)
(Continued)

(52) U.S. Cl.
CPC .......... *A61B 8/4245* (2013.01); *A61B 5/4869* (2013.01); *A61B 8/429* (2013.01);
(Continued)

(58) Field of Classification Search
None
See application file for complete search history.

(56) References Cited

U.S. PATENT DOCUMENTS

| 4,899,757 A | * | 2/1990 | Pope, Jr. | ............... | A61B 8/06 600/463 |
| 6,057,927 A | | 5/2000 | Lévesque et al. | | |

(Continued)

FOREIGN PATENT DOCUMENTS

| EP | 0980210 | 2/2000 |
| EP | 1815796 | 8/2007 |

OTHER PUBLICATIONS

USPTO, Office Action for U.S. Appl. No. 13/497,648, dated Jun. 20, 2013.

(Continued)

*Primary Examiner* — James M Kish
(74) *Attorney, Agent, or Firm* — Hodgson Russ LLP (57) ABSTRACT

A method and a device for nondestructively detecting an elasticity of a viscoelastic medium are provided. The method includes: driving an ultrasonic transducer probe with a low-frequency vibration by a vibrator so as to produce an elastic wave in the viscoelastic medium; producing an ultrasonic wave by the ultrasonic transducer probe, and transmitting the ultrasonic wave to the viscoelastic medium; collecting an ultrasonic echo when the elastic wave is propagated in the viscoelastic medium and the ultrasonic transducer probe stops or almost stops vibrating; calculating an elastic parameter of the viscoelastic medium according to the collected ultrasonic echo.

17 Claims, 2 Drawing Sheets (51) Int. Cl.
  *A61B 8/08* (2006.01)
  *G01N 29/07* (2006.01)
  *G01N 29/34* (2006.01)
  *A61B 6/00* (2006.01)

(52) U.S. Cl.
  CPC .......... *A61B 8/4218* (2013.01); *A61B 8/4405* (2013.01); *A61B 8/4416* (2013.01); *A61B 8/4477* (2013.01); *A61B 8/461* (2013.01); *A61B 8/467* (2013.01); *A61B 8/483* (2013.01); *A61B 8/485* (2013.01); *A61B 8/486* (2013.01); *A61B 8/5207* (2013.01); *A61B 8/5223* (2013.01); *A61B 8/54* (2013.01); *G01N 29/07* (2013.01); *G01N 29/348* (2013.01); *A61B 6/487* (2013.01); *G01N 2291/02466* (2013.01); *G01N 2291/02827* (2013.01)

(56) References Cited

U.S. PATENT DOCUMENTS

| | | | |
|---|---|---|---|
| 6,063,031 A * | 5/2000 | Cundari | A61B 5/0053 600/439 |
| 6,364,028 B1 | 4/2002 | Ferrell et al. | |
| 6,770,033 B1 | 8/2004 | Fink et al. | |
| 7,357,028 B2 | 4/2008 | Kim | |
| 2005/0119568 A1 | 6/2005 | Salcudean et al. | |
| 2005/0203398 A1* | 9/2005 | Sandrin | A61B 5/0048 600/438 |
| 2006/0173320 A1* | 8/2006 | Radulescu | A61B 8/08 600/438 |
| 2006/0211942 A1 | 9/2006 | Hoctor et al. | |
| 2007/0016037 A1 | 1/2007 | Houle et al. | |
| 2007/0232916 A1* | 10/2007 | Waki | A61B 5/6843 600/444 |
| 2009/0012399 A1 | 1/2009 | Sunagawa et al. | |
| 2009/0073453 A1 | 3/2009 | Hasegawa | |
| 2009/0088639 A1* | 4/2009 | Maschke | A61B 8/4218 600/443 |

OTHER PUBLICATIONS

USPTO, Office Action for U.S. Appl. No. 13/497,648, dated Feb. 4, 2014.

USPTO, Office Action for U.S. Appl. No. 13/497,648, dated Nov. 17, 2014.

* cited by examiner

METHOD AND DEVICE FOR DETECTING ELASTICITY OF VISCOUS ELASTIC MEDIUM

FIELD

The present disclosure relates to a nondestructive measurement field, and more particularly to a method for detecting an elasticity of a viscoelastic medium and a device for detecting an elasticity of a viscoelastic medium which will produce a scattering signal after irradiated by an ultrasonic wave.

BACKGROUND

A technology for nondestructively measuring a viscoelastic medium is very important in a food industry field. If an elasticity of a food may be conveniently detected, a quality of the food will be better controlled. In addition, in a medical field, various chronic liver diseases (e.g., virus hepatitis, alcoholic hepatitis, nonalcoholic steatohepatitis, autoimmune liver disease) will lead to hepatic fibrosis and hepatic cirrhosis. An elasticity of a liver will change during hepatic fibrosis and hepatic cirrhosis. If the elasticity of the liver may be nondestructively detected, conditions of the liver disease may be monitored and estimated so as to take effective treatment in time.

Chinese patent (publication No. CN1674827) discloses a device and a method for measuring an elasticity of a human or animal organ. The device comprises an ultrasonic transducer probe, a position sensor, an actuator, and a controlled electrodynamic actuator that generates a transitory low-frequency impulse. The device uses an ultrasonic wave at an ultra-high pulse frequency to detect a propagation velocity of an elastic wave produced by the transitory low-frequency impulse generated by the controlled electrodynamic actuator in a viscoelastic medium. Therefore, the elasticity of the viscoelastic medium may be obtained using an intrinsic relationship between the propagation velocity of the elastic wave and the elasticity of the viscoelastic medium.

In the above device, the electrodynamic actuator drives the ultrasonic transducer probe to generate a low-frequency vibration, thus introducing the elastic wave in the viscoelastic medium. The ultrasonic transducer probe transmits and collects the ultrasonic wave while generating a mechanical vibration, which may cause a reference point for collecting data of the ultrasonic wave to move. Therefore, before a further calculation using the data, a motion may need to be compensated. The device detects a motion of the ultrasonic transducer probe by the position sensor so as to compensate the motion of the ultrasonic transducer probe. Although the method may solve a problem of movement of the reference point by motion compensation, it may need extra calculation time. Meanwhile, because the position sensor needs to be mounted, a complexity and a cost of a system are increased.

In addition, the above device relies on manual operation, and consequently measurement results will be influenced by a pressure applied to the viscoelastic medium by the ultrasonic transducer probe and a verticality between the ultrasonic transducer probe and the viscoelastic medium in operation. In practical operation, an operator needs to determine whether the pressure applied to the viscoelastic medium and the verticality between the ultrasonic transducer probe and the viscoelastic medium are suitable empirically, so that detecting results will be easily influenced by subjective factors of the operator. Therefore, it is possible to cause large differences between results under operations of different operators or different operations of the same operator.

In addition, with the above device, a final result may be usually obtained by measuring the same position many times. Because the operator holds the ultrasonic transducer probe by hand during measurement, it is very difficult to ensure that all measurements are performed in the same position, which may also influence an accuracy of the result.

SUMMARY

The present disclosure is directed to solve at least one of the problems existing in the prior art. Accordingly, for a viscoelastic medium which may scatter an ultrasonic signal, especially an organ or a tissue of a human or an animal, a method for nondestructively detecting an elasticity of a viscoelastic medium and a device for nondestructively detecting an elasticity of a viscoelastic medium are provided, which may be less influenced by subjective factors of an operator without motion compensation.

According to an aspect of the present disclosure, a method for detecting an elasticity of a viscoelastic medium is provided. The method comprises steps of: a) driving an ultrasonic transducer probe with a low-frequency vibration by a vibrator so as to produce an elastic wave to be propagated in the viscoelastic medium, transmitting an ultrasonic wave to the viscoelastic medium by the ultrasonic transducer probe at a pulse repetition frequency of about 100 Hz-100000 Hz, and collecting an ultrasonic echo returned from the viscoelastic medium; b) selecting an effective ultrasonic echo from the ultrasonic echo according to a duration of the low-frequency vibration and physical parameters of the viscoelastic medium, wherein the ultrasonic transducer probe is static and the elastic wave is propagated in the viscoelastic medium at a moment corresponding to the effective ultrasonic echo; c) calculating a propagation velocity of the elastic wave in the viscoelastic medium according to the effective ultrasonic echo; and d) calculating the elasticity of the viscoelastic medium according to the propagation velocity of the elastic wave.

According to another aspect of the present disclosure, a device for detecting an elasticity of a viscoelastic medium is provided. The device comprises: a vibrator producing a low-frequency vibration; an ultrasonic transducer probe driven by the vibrator with the low-frequency vibration so as to produce an elastic wave to be propagated in the viscoelastic medium; and a control apparatus connected with the ultrasonic transducer probe and the vibrator respectively, and configured to control the ultrasonic transducer probe to transmit an ultrasonic wave to the viscoelastic medium and to collect an ultrasonic echo returned from the viscoelastic medium, to select an effective ultrasonic echo from the ultrasonic echo according to a duration of the low-frequency vibration and physical parameters of the viscoelastic medium, and to calculate a propagation velocity of the elastic wave in the viscoelastic medium according to the effective ultrasonic echo to calculate the elasticity of the viscoelastic medium, wherein the ultrasonic transducer probe is static and the elastic wave is propagated in the viscoelastic medium at a moment corresponding to the effective ultrasonic echo.

The features and the beneficial effects of the present disclosure are as follows.

A time period is selected according to a duration of the low-frequency vibration and parameters such as a thickness, a hardness range or a density of the viscoelastic medium, within which the elastic wave produced by the low-frequency vibration is still propagated in the viscoelastic medium but the ultrasonic transducer probe transmitting the ultrasonic wave is static or nearly static. Because the ultrasonic transducer probe may be considered to be static, a reference point for ultrasonic echo data collected within the time period may be considered to be static. Subsequent calculations may be performed using the ultrasonic echo data collected within the time period, without the need of ultrasonic probe motion compensation, thus reducing a calculation time. Meanwhile, a position sensor to detect a motion of the ultrasonic probe is not required, thus reducing a complexity and a cost of a system. Compared with a device and a method for measuring an elasticity of a human or animal organ disclosed in the above patent (publication No. CN1674827), with the method for detecting the elasticity of the viscoelastic medium and the device for detecting the elasticity of the viscoelastic medium according to an embodiment of the present disclosure, a function of measuring the elasticity of the viscoelastic medium may be also achieved, without the position sensor. The complexity and the cost of the device may be reduced by omitting members.

An average pressure applied to the ultrasonic transducer probe may be measured by a pressure sensor array comprised in the device. When the pressure sensor array comprises three or more pressure sensors, a verticality between the ultrasonic transducer probe and a surface of the viscoelastic medium may be obtained using a pressure difference detected by different sensors in the pressure sensor array. Moreover, by adding a step of determining whether a pressure applied to the viscoelastic medium by the ultrasonic transducer probe is suitable and a step of determining whether a verticality between the ultrasonic transducer probe and the viscoelastic medium is suitable in the method, limitations of empirically determining whether the pressure and the verticality are suitable by the operator in a conventional device may be overcome, thus reducing the influence of subjective factors on elasticity measurement and improving the success rate and accuracy of a measurement.

In addition, the device may further comprise a mechanical arm for supporting an ultrasonic probe. In this way, once a detecting position is selected, it may be ensured that all the detections are performed in the same position, thus improving a repeatability of the measurement. Meanwhile, with the help of the mechanical arm, the implementation of semi-automatic or fully automatic operation may be facilitated, thus reducing the burden of the operator.

Additional aspects and advantages of the embodiments of the present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of the disclosure will become apparent and more readily appreciated from the following descriptions taken in conjunction with the drawings in which.

DETAILED DESCRIPTION

Embodiments of the present disclosure will be described in detail in the following descriptions, examples of which are shown in the accompanying drawings, in which the same or similar elements and elements having same or similar functions are denoted by like reference numerals throughout the descriptions. The embodiments described herein with reference to the accompanying drawings are explanatory and illustrative, which are used to generally understand the present disclosure. The embodiments shall not be construed to limit the present disclosure.

A method for detecting an elasticity of a viscoelastic medium and a device for detecting an elasticity of a viscoelastic medium according to an embodiment of the present disclosure will be described below in detail with reference to the drawings.

The method for detecting the elasticity of the viscoelastic medium according to an embodiment of the present disclosure comprises steps of:

a) driving an ultrasonic transducer probe with a low-frequency vibration by a vibrator so as to produce an elastic wave to be propagated in the viscoelastic medium, transmitting an ultrasonic wave to the viscoelastic medium by the ultrasonic transducer probe at a pulse repetition frequency of about 100 Hz-100000 Hz, and collecting an ultrasonic echo returned from the viscoelastic medium;

b) selecting an effective ultrasonic echo from the ultrasonic echo according to a duration of the low-frequency vibration and physical parameters of the viscoelastic medium, in which the ultrasonic transducer probe is static and the elastic wave is propagated in the viscoelastic medium at a moment corresponding to the effective ultrasonic echo;

c) calculating a propagation velocity of the elastic wave in the viscoelastic medium according to the effective ultrasonic echo; and d) calculating the elasticity of the viscoelastic medium according to the propagation velocity of the elastic wave.

The method may also comprise a step of preselecting a detecting region, which helps to select a suitable position to detect the elasticity of the viscoelastic medium. For example, for detecting an elasticity of a liver, the step of preselecting the detected region may help to keep away from large vessels of the liver so as to avoid an influence on results of detecting of the elasticity of the viscoelastic medium.

A vibration frequency f of the low-frequency vibration is between about 0.5 Hz and about 3000 Hz, and the duration T of the low-frequency vibration is between about ½ f and about 40/f.

Preferably, the method may comprise a step of determining whether a pressure applied to the viscoelastic medium by the ultrasonic transducer probe is suitable.

Preferably, the method may comprise a step of determining whether a verticality between the ultrasonic transducer probe and the viscoelastic medium is suitable.

The device for detecting the elasticity of the viscoelastic medium according to an embodiment of the present disclosure comprises:

a vibrator producing a low-frequency vibration;

an ultrasonic transducer probe driven by the vibrator with the low-frequency vibration so as to produce an elastic wave to be propagated in the viscoelastic medium; and a control apparatus connected with the ultrasonic transducer probe and the vibrator respectively, and configured to control the ultrasonic transducer probe to transmit an ultrasonic wave to the viscoelastic medium and to collect an ultrasonic echo returned from the viscoelastic medium, to select an effective ultrasonic echo from the ultrasonic echo according to a duration of the low-frequency vibration and physical parameters of the viscoelastic medium, and to calculate a propagation velocity of the elastic wave in the viscoelastic medium according to the effective ultrasonic echo to calculate the elasticity of the viscoelastic medium, in which the ultrasonic transducer probe is static and the ultrasonic wave is propagated in the viscoelastic medium at a moment corresponding to the effective ultrasonic echo. It should be noted that in some embodiments, "the ultrasonic transducer probe is static" means that the ultrasonic transducer probe is substantially or nearly static.

Because the ultrasonic transducer probe is configured to transmit the ultrasonic wave to the viscoelastic medium and to collect the ultrasonic echo returned from the viscoelastic medium under a control of the control apparatus, when the ultrasonic transducer probe is used for detecting the elasticity of the liver, in order to transmit the ultrasonic wave and to receive the ultrasonic echo through a intercostal space in a human body, a largest outer diameter of an end face of the ultrasonic transducer probe should be less than about 12 mm.

The control apparatus may comprise one of a computer, a microprocessor and a microcontroller having a user interaction device, as well as an ultrasonic transmitting and receiving circuit (which is well known to those skilled in the art) connected with the one of the computer, the microprocessor and the microcontroller through a communication interface (e.g., USB, PCI). The control apparatus may also comprise a triggering key implemented by a hardware or a software for starting to detect the elasticity of the viscoelastic medium.

The user interaction device comprised in the control apparatus may be configured to input information and display detecting results. The user interaction device may be constituted by a mouse, a keyboard and a display, and may also be constituted by a touch screen or other user interaction devices.

The ultrasonic transmitting and receiving circuit comprised in the control apparatus may transmit the ultrasonic waves through the ultrasonic transducer probe at a pulse repetition frequency of about 1 Hz-100000 Hz and collect the ultrasonic echoes according to requirements under a control of the computer, the microprocessor or the microcontroller comprised in the control apparatus.

The vibrator may produce a low-frequency vibration with a frequency of about 0.5 Hz-3000 Hz and an amplitude of 0.5 mm-20 mm. The vibrator may accurately produce a required low-frequency vibration according to a required starting time, a required waveform and a required amplitude under the control of the control apparatus. Because the ultrasonic transducer probe is connected with the vibrator, the vibration may be transmitted to the viscoelastic medium through the ultrasonic transducer probe.

Under a unified control of the control apparatus, once an operator uses the triggering key to start to detect the elasticity of the viscoelastic medium, the vibrator will drive the ultrasonic transducer probe to produce a low-frequency vibration so as to produce a low-frequency elastic wave to be propagated in the viscoelastic medium; and the ultrasonic transmitting and receiving circuit may transmit the ultrasonic wave at a pulse repetition frequency of about 100 Hz-100000 Hz and collect the ultrasonic echo. The control apparatus may be configured to calculate the elasticity of the viscoelastic medium using the ultrasonic echo. Particularly, the ultrasonic echo scattered back from the viscoelastic medium may be used for tracking a propagation of the elastic wave in the viscoelastic medium so as to calculate the propagation velocity of the elastic wave in the viscoelastic medium, and then the elasticity of the viscoelastic medium may be calculated using an intrinsic relationship between the propagation velocity of the elastic wave and the elasticity and a density of the viscoelastic medium.

In one embodiment, the device for detecting the elasticity of the viscoelastic medium according to an embodiment of the present disclosure may further comprise an ultrasonic diagnostic equipment. The ultrasonic diagnostic equipment may be a conventional B-mode ultrasonic diagnostic equipment or a color Doppler ultrasonic diagnostic equipment. With the help of a two-dimensional or three-dimensional ultrasonic imaging probe of the ultrasonic diagnostic equipment, a two-dimensional or three-dimensional ultrasonic image may be provided on a user interface, thus providing pre-scanning and pre-positioning for the detecting of the elasticity of the viscoelastic medium.

In another embodiment, the device for detecting the elasticity of the viscoelastic medium according to an embodiment of the present disclosure may further comprise a pressure sensor array. At this time, the control apparatus further comprises a pressure signal collecting circuit (which is well known to those skilled in the art) connected with one of the computer, the microprocessor and the microcontroller through a communication interface (e.g., USB, PCI). The pressure sensor array comprises at least one pressure sensor. The pressure sensor array contacts the ultrasonic transducer probe and the vibrator, and may be configured to detect an average pressure applied to the ultrasonic transducer probe in operation and to feed the pressure information back to the operator so that the operator may apply a suitable pressure, thus improving an accuracy of a measurement.

Preferably, the pressure sensor array comprises three pressure sensors. The average pressure applied to the ultrasonic transducer probe may be obtained using pressure values detected by the pressure sensors in the pressure sensor array, and it may be determined whether the ultrasonic transducer probe is nearly vertical to a surface of the viscoelastic medium using a difference between pressure values detected by the pressure sensors in the pressure sensor array. The information is fed back to the operator, thus helping the operator implement accurate and repeatable measurement.

The device for detecting the elasticity of the viscoelastic medium according to an embodiment of the present disclosure may comprise at least one mechanical arm for supporting an ultrasonic probe consisting of the ultrasonic transducer probe and the vibrator. Meanwhile, in order to help the operator select a detecting position flexibly, the mechanical arm is configured to have at least one degree of freedom. The ultrasonic probe may be fixed on the mechanical arm. When the operator pulls the mechanical arm by hand, a detecting position may be flexibly selected. After the detecting position is selected, the operator lets loose the hand, and the ultrasonic probe may be fixed on the selected position, thus ensuring that all the detections are performed in the same position. Meanwhile, with the help of the mechanical arm, the implementation of a semi-automatic or fully automatic operation may be achieved, thus reducing the burden of the operator.

The device for detecting the elasticity of the viscoelastic medium according to an embodiment of the present disclosure may further comprise a state indicating device for indicating a working state of the device. The operator may conveniently know the working state of the device according to the state indicating device.

The device for detecting the elasticity of the viscoelastic medium according to an embodiment of the present disclosure may further comprise an elastic intermediate medium. The operator places the elastic intermediate medium between the viscoelastic medium and the ultrasonic transducer probe when detecting the elasticity of the viscoelastic medium, thus ensuring that the elastic wave is still propagated in the viscoelastic medium when the ultrasonic probe stops vibrating.

Figure 1:
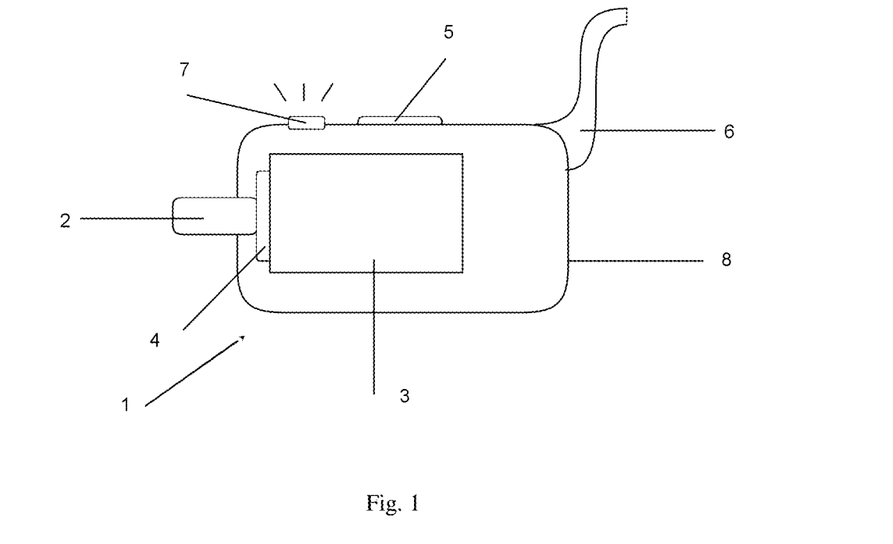
FIG. 1 is a schematic diagram of a device for detecting an elasticity of a viscoelastic medium according to an embodiment of the present disclosure.

As shown in FIG. 1, in one preferred embodiment, the device for detecting the elasticity of the viscoelastic medium comprises an ultrasonic probe 1 consisting of the ultrasonic transducer probe 2, the vibrator 3 and the pressure sensor array 4. The ultrasonic transmitting and receiving circuit (not shown) is configured to transmit the ultrasonic wave and to collect the ultrasonic echo through the ultrasonic transducer probe 2. The ultrasonic transducer probe 2 and the vibrator 3 are fixed together through the pressure sensor array 4. The ultrasonic probe 1 is mounted in a shell 8 formed with the state indicating device 7. An end portion of the shell 8 is formed with a cable 6 connected with the ultrasonic probe 1. The control apparatus (not shown) is connected with the ultrasonic probe 1 and the state indicating device 7 through the cable 6, and it comprises a key 5 fixed on the shell 8. In other embodiments, the pressure sensor array 4 and the state indicating device 7 may be omitted.

Functions and particular components of the above members are illustrated below in detail respectively.

The function of the control apparatus is to start to detect the elasticity of the viscoelastic medium by the key 5, to control the work of the vibrator 3 and the state of the state indicating device 7, and to control the ultrasonic transducer probe 2 to transmit the ultrasonic wave and collect the ultrasonic echo. The control apparatus may further control a signal collection of the pressure sensors, process data of the ultrasonic echo and the pressure, and display results. The control apparatus may comprise a computer, a microcontroller or a microprocessor having a display 11 and a keyboard 12 (for example, a DELL Optiplex 360 desktop computer, an ARM Cortex-A8 microcontroller from Arm company or a Pentium III processor from Intel corporation) as well as an ultrasonic transmitting and receiving circuit and a pressure signal collecting circuit (which are well known to those skilled in the art) connected with the one of the computer, the microprocessor and the microcontroller through communication interfaces (e.g., USB, PCI) respectively.

Figure 2:
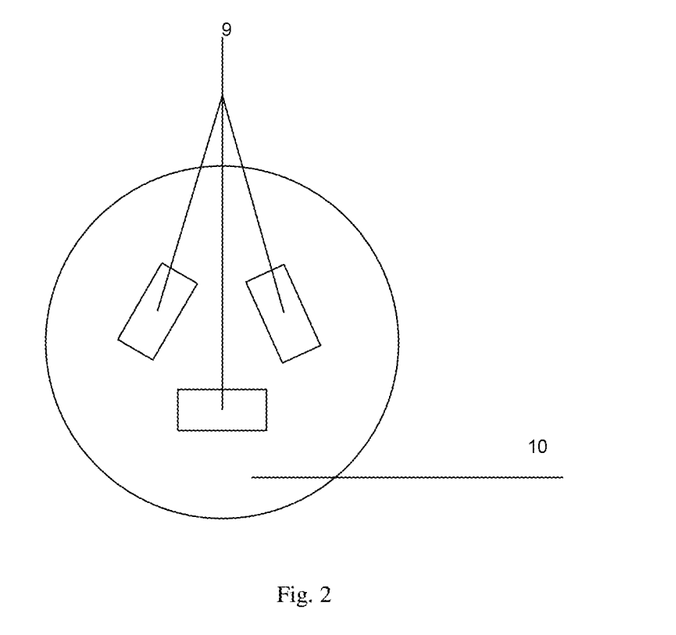
FIG. 2 is a schematic diagram of a pressure sensor array comprised in the device in FIG. 1.

The pressure sensor array 4 may be configured to detect the pressure applied to the viscoelastic medium and the verticality between the ultrasonic transducer probe 2 and the surface of the viscoelastic medium. A top view of the pressure sensor array 4 is shown in FIG. 2, and the pressure sensor array 4 may comprise three small Model F pressure sensors 9 from Honeywell International Inc. which are mounted at centers of sides of a right triangle on a circuit board 10 respectively.

The state indicating device 7 is configured to indicate the working state of the device and may be constituted by a set of LED lamps having different colors.

In some embodiments, the ultrasonic transducer probe 2 is configured to transmit the ultrasonic waves to the viscoelastic medium and to collect the ultrasonic echoes under a control of the control apparatus. In practical application, an ultrasonic transducer probe with a corresponding central frequency and a corresponding size may be selected according to characteristics of the viscoelastic medium and precision requirements. For example, when the viscoelastic medium is a liver of a human body, an ultrasonic transducer probe with a central frequency of about 1 MHz-15 MHz may be selected, and a largest outer diameter of an end face of the ultrasonic transducer probe should be less than about 12 mm so that the ultrasonic transducer probe may transmit the ultrasonic wave and receive the ultrasonic echo through a intercostal space in a human body.

The function of the vibrator 3 is to drive the ultrasonic transducer probe 2 to produce a low-frequency vibration under the control of the control apparatus. The vibrator 3 may produce a low-frequency vibration with a frequency of about 0.5 Hz-3000 Hz and an amplitude of about 0.5 mm-20 mm under the control of the control apparatus. Particularly, the vibrator 3 may be an electromagnetic type vibrator or a stepping motor type vibrator.

The key 5 on the shell 8 as a part of the control apparatus is configured to start the vibrator 3 to produce a low-frequency vibration and to start the ultrasonic transmitting and receiving circuit of the control apparatus to transmit the ultrasonic wave at a pulse repetition frequency of about 100 Hz-100000 Hz and to collect the ultrasonic echo.

The shell 8 is used for protecting members inside the shell 8, and may be made of ABS plastics.

When the elasticity of the viscoelastic medium is detected, the viscoelastic medium is scanned by the ultrasonic transducer probe 2 of the ultrasonic probe 1. At this time, the ultrasonic transmitting and receiving circuit of the control apparatus triggers the ultrasonic transducer probe 2 to transmit the ultrasonic wave at a pulse repetition frequency within about 100 Hz (for example, 30 Hz) and to collect the ultrasonic echo. The computer, the microprocessor or the microcontroller of the control apparatus performs envelop calculation, logarithmic compression, etc. for the ultrasonic echo, and then display results in the form of a M-mode ultrasonograph (well known to those skilled in the art, with a full name of a motion mode ultrasonograph) on the display. The operator may acquire information of the viscoelastic medium so as to select a position to detect the elasticity of the viscoelastic medium. Preferably, when the ultrasonic echo is collected, the pressure information from the pressure sensors are collected by the pressure signal collecting circuit of the control apparatus, and the computer, the microprocessor or the microcontroller of the control apparatus determines whether the pressure applied to the ultrasonic transducer probe 2 or the verticality between the ultrasonic transducer probe 2 and the viscoelastic medium is suitable.

When a suitable position to detect the elasticity of the viscoelastic medium is selected and it is determined that the pressure applied to the ultrasonic transducer probe 2 or the verticality between the ultrasonic transducer probe 2 and the viscoelastic medium is suitable, the operator may trigger the key 5, and the vibrator 3 will drive the ultrasonic transducer probe 2 to produce a low-frequency vibration with a frequency of about 0.5 Hz-3000 Hz and an amplitude of about 0.5 mm-20 mm (for example, with a frequency of 50 Hz and an amplitude of 2 mm) which may produce an elastic wave to be propagated in the viscoelastic medium. Meanwhile, a triggering signal will trigger the ultrasonic transmitting and receiving circuit of the control apparatus to transmit the ultrasonic wave at a pulse repetition frequency of about 100 Hz-100000 Hz (for example, 6000 Hz) and to collect the ultrasonic echo. The computer, the microprocessor or the microcontroller of the control apparatus calculates the elasticity of the viscoelastic medium using the ultrasonic echo.

Figure 3:
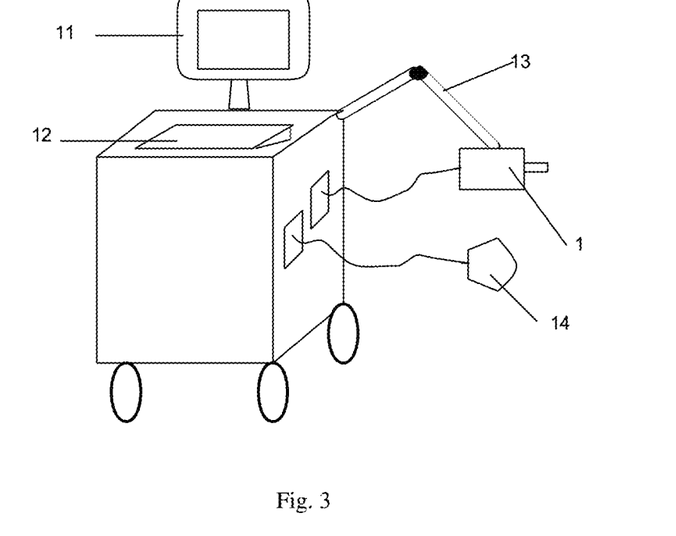
FIG. 3 is a schematic diagram of a device for detecting an elasticity of a viscoelastic medium which further comprising an ultrasonic diagnostic equipment and a mechanical arm according to an embodiment of the present disclosure.

The above-mentioned device may also be integrated with an ultrasonic diagnostic equipment. As shown in FIG. 3, the control apparatus and the ultrasonic diagnostic equipment (not shown) are mounted inside a box, the keyboard 12 and the display 11 of the control apparatus are mounted outside the box, and the ultrasonic probe 1 and the two-dimensional or three-dimensional imaging probe 14 comprised in the ultrasonic diagnostic equipment are connected with the box through cables respectively. Using the two-dimensional or three-dimensional imaging probe 14 comprised in the ultrasonic diagnostic equipment, imaging of the viscoelastic medium may be performed to acquire more information, thus helping to keep away from regions affecting elasticity measurement during elasticity measurement (for example, keep away from large vessels in a liver when a liver of a human body is measured).

In the above-mentioned device, a mechanical arm 13 may also be mounted on the box for supporting the ultrasonic probe 1, and may have at least one degree of freedom. When the operator pulls the mechanical arm 13, a detecting position may be flexibly selected. After the detecting position is selected, the operator lets loose the hand, and the ultrasonic probe 1 may be fixed on the selected position, thus ensuring that all the detections are in the same position.

The method for detecting the elasticity of the viscoelastic medium according to an embodiment of the present disclosure comprises the following steps.

(a) The ultrasonic probe 1 is placed on the viscoelastic medium, and a position to detect the elasticity of the viscoelastic medium is selected using the M-mode ultrasonograph of the viscoelastic medium acquired by the ultrasonic probe 1, an ultrasonic image of the viscoelastic medium acquired by the ultrasonic imaging probe 14 comprised in the ultrasonic diagnostic equipment, or both after the ultrasonic transducer probe 2 contacts the viscoelastic medium (this step is a preferred step).

(b) It is determined whether the pressure applied to the viscoelastic medium by the ultrasonic probe 1 is suitable using pressure data detected by the pressure sensor array 4 (this step is a preferred step). In this embodiment, the pressure sensor array 4 comprises three pressure sensors, and the pressures detected by the three pressure sensors are $F_1$, $F_2$, and $F_3$ respectively. It is determined whether the pressure applied to the viscoelastic medium by the ultrasonic probe 1 is suitable according to the following formulae:

$$F=(F_1+F_2+F_3)/3 \quad (1)$$

$$F_{min}<F<F_{max} \quad (2).$$

That is, an average pressure F applied to the viscoelastic medium by the ultrasonic probe 1 is calculated according to the formula (1), and then it is determined whether the average pressure F is suitable according to the formula (2), where $F_{min}$ and $F_{max}$ are a lower limit and an upper limit of the average pressure F respectively. For measurement of an elasticity of a soft tissue of an animal or human body, $F_{min}$ may be about 1 newton, and $F_{max}$ may be about 10 newtons.

(c) It is determined whether a verticality between the ultrasonic probe 1 and the viscoelastic medium is suitable using pressure data detected by the pressure sensor array 4 (this step is a preferred step). In this embodiment, it is determined whether the verticality between the ultrasonic probe 1 and the viscoelastic medium is suitable according to the following formulae:

$$\delta=(|F_1-F|+|F_2-F|+|F_3-F|)/3F \quad (3)$$

$$\delta<\delta_{max} \quad (4).$$

$\delta$ calculated according to the formula (3) represents a difference between pressures applied to the pressure sensors in the pressure sensor array 4. Very small $\delta$ indicates that the pressures applied to the pressure sensors are substantially the same and the ultrasonic probe 1 is nearly vertical to the viscoelastic medium. The larger the $\delta$, the larger the difference between pressures applied to the pressure sensors is, and the lower the verticality between the ultrasonic probe 1 and the viscoelastic medium is. $\delta_{max}$ is a threshold which indicates an acceptable degree deviating from a vertical direction when the elasticity of the viscoelastic medium is detected. For measurement of an elasticity of a soft tissue of an animal or human body, $\delta_{max}$ may be about 0.1.

(d) The ultrasonic probe 1 may produce a low-frequency vibration with an amplitude of about 2 mm, a frequency $f_0$ of about 50 Hz and a duration T of about 0.05 s. The elastic wave produced by the low-frequency vibration will propagate from a surface of the viscoelastic medium to a deep part of the viscoelastic medium at a propagation velocity related to a hardness of the viscoelastic medium. When the low-frequency vibration is produced, the ultrasonic transmitting and receiving circuit of the control apparatus transmits the ultrasonic wave to the viscoelastic medium at a pulse repetition frequency $F_{high}$ of about 6000 Hz and collects an ultrasonic signal scanning line (in the art, a collected ultrasonic echo corresponding to an transmitted ultrasonic pulse is called one ultrasonic signal scanning line). Serial numbers of the ultrasonic signal scanning lines are recorded as 1, 2, 3, . . . N . . . respectively, in which a time interval between the ultrasonic signal scanning lines is $\Delta t=1/F_{high}$, where N is a positive integer.

(e) A range of the ultrasonic echo (i.e., an effective ultrasonic echo) used for subsequent calculation is selected from the ultrasonic echo according to a duration of the low-frequency vibration and physical parameters (e.g., a thickness, a hardness range, a density) of the viscoelastic medium. The effective ultrasonic echo may be selected by selecting ranges of serial numbers of the ultrasonic signal scanning lines. In the present disclosure, the selected ultrasonic signal scanning lines are called effective ultrasonic signal scanning lines. The principle of the selecting is that the ultrasonic transducer probe is static or nearly static and the elastic wave is still propagated in the viscoelastic medium at a moment corresponding to the ultrasonic signal scanning lines in the selected ranges of serial numbers of the ultrasonic signal scanning lines.

In some embodiments, a method for selecting the ultrasonic signal scanning lines is as follows.

When the duration of the low-frequency vibration is T, in consideration of an inertia of the vibration, assume that the ultrasonic transducer probe is static after T+$\Delta$T since the vibration starts, a serial number $N_{select}$ of an effective ultrasonic signal scanning line should satisfy:

$$N_{select} \geq \text{ceiling}((T+\Delta T) \times F_{high}) \quad (5)$$

where ceiling(.) is a ceiling rounding function, and $N_{select}$ is a natural number.

Assuming a thickness of the viscoelastic medium is $D_1$, and a lower limit of the propagation velocity of the elastic wave in the viscoelastic medium determined according to an estimated hardness range and an estimated density of the viscoelastic medium is $V_s^1$, when the elastic wave is still propagated in the viscoelastic medium, the serial number $N_{select}$ of the effective ultrasonic signal scanning line should satisfy:

$$N_{select} \leq \text{ceiling}((D_1/V_s^1+T) \times F_{high}) \quad (6).$$

When $\Delta T$ is less than $D_1/V_s^1$, by combining above two formulae, $N_{select}$ may satisfy:

$$\text{ceiling}((T+\Delta T) \times F_{high}) \leq N_{select} \leq \text{ceiling}((D_1/V_s^1+T) \times F_{high}) \quad (7).$$

For example, when $\Delta T$ is 0.01 s, the lower limit $V_s^1$ of the propagation velocity of the elastic wave in the viscoelastic medium is 3 m/s, and the thickness $D_1$ of the viscoelastic medium is 10 cm, the range of the serial number of the ultrasonic signal scanning line is $360 \leq N_{select} \leq 500$.

Figure 4:
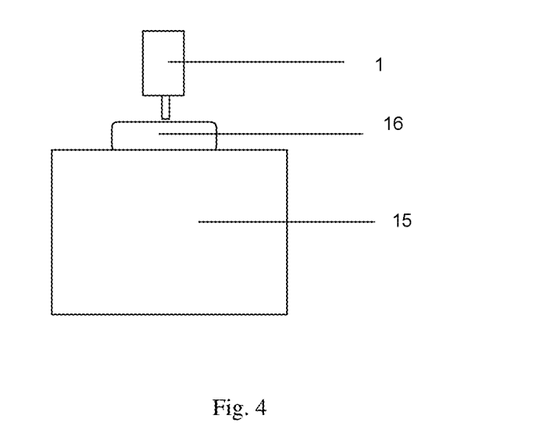
FIG. 4 is a schematic diagram of an elastic intermediate medium added between a viscoelastic medium and a device for detecting an elasticity of a viscoelastic medium according to an embodiment of the present disclosure.

When $\Delta T$ is not less than $D_1/V_s^1$, as shown in FIG. 4, if an elastic intermediate medium 16 with a thickness of $D_2$ is added between the ultrasonic transducer probe 2 of the ultrasonic probe 1 and the viscoelastic medium 15 so that $\Delta T < D_1/V_s^1 + D_2/V_s^2$, where $V_s^2$ is a propagation velocity of the elastic wave in the elastic intermediate medium, then the serial number $N_{select}$ of the effective ultrasonic signal scanning line should satisfy:

$$\text{ceiling}((T+\Delta T) \times F_{high}) \leq N_{select} \leq \text{ceiling}((D_2/V_s^2+D_1/V_s^1+T) \times F_{high}) \quad (8).$$

For example, when $\Delta T$ is 0.01 s, the lower limit $V_s^1$ of the propagation velocity of the elastic wave in the viscoelastic medium is 3 m/s, the thickness $D_1$ of the viscoelastic medium is 10 cm, the thickness $D_2$ of the elastic intermediate medium is 10 cm, and the propagation velocity $V_s^2$ of the elastic wave in the viscoelastic medium is 1 m/s, the range of the serial number of the ultrasonic signal scanning line is $360 \leq N_{select} \leq 960$.

(f) The propagation velocity of the elastic wave in the viscoelastic medium is calculated according to the effective ultrasonic echo.

In this embodiment, the propagation velocity of the elastic wave is calculated using a linear regression of a propagation of a phase of a strain introduced in the viscoelastic medium by the low-frequency elastic wave at the central frequency of the vibration in a depth direction along with time.

First, the strain introduced in the viscoelastic medium by the low-frequency elastic wave needs to be calculated. The strain in the viscoelastic medium may be calculated by first estimating a displacement of the viscoelastic medium and then differentiating using the displacement of the viscoelastic medium. A particular calculation method is well known to those skilled in the art, which will be described below in detail.

The displacement of the viscoelastic medium may be estimated by a displacement estimation method well known to those skilled in the art, for example, a cross correlation method, an absolute difference sum method, a Doppler method, or a self correlation method. In this embodiment, the displacement of the viscoelastic medium is estimated by a cross correlation method.

Assuming each ultrasonic signal scanning line has data of L points, an actual distance corresponding to two adjacent data points is $\Delta z$, each ultrasonic signal scanning line may be divided into L−2m data segments with a length of 2m+1 with an interval of 1 point for center of each segment, and the centers of the L−2m data segments are m+1, m+2, . . . , L−m points on each ultrasonic signal scanning line respectively, a correlation coefficient between a data segment with a p point as a center on a $n_1^{th}$ ultrasonic signal scanning line and a data segment with a q point as a center on a $(n_1+1)^{th}$ ultrasonic signal scanning line is calculated by the following formula:

$$C_{p,q} = \frac{\sum_{i=-m}^{m} r_{n_1}(p+i) r_{n_1+1}(q+i)}{\sqrt{\sum_{i=-m}^{m} (r_{n_1}(p+i))^2 \sum_{i=-m}^{m} (r_{n_1+1}(q+i))^2}} \quad (9)$$

where $r_{n_1}$ and $r_{n_1+1}$ represent data on the $n_1^{th}$ ultrasonic signal scanning line and the $(n_1+1)^{th}$ ultrasonic signal scanning line respectively.

The following maximal value $C_{p,q_{max}}$ of the correlation coefficients is obtained by calculating correlation coefficients between the data segment with the p point as a center on the $n_1^{th}$ ultrasonic signal scanning line and all data segments on the $(n_1+1)^{th}$ ultrasonic signal scanning line and searching:

$$C_{p,q_{max}} = \max\{C_{p,q}, q=m+1, m+2, \ldots, L-m\} \quad (10)$$

Therefore, a displacement of a medium fragment with a center at a $p \cdot \Delta z$ depth and a length of $(2m+1) \cdot \Delta z$ during a duration between a time $n_1 \cdot \Delta t$ and a time $(n_1+1) \cdot \Delta t$ is as follows:

$$d(z,t)|_{z=p \cdot \Delta z, t=n_1 \cdot \Delta t} = (q_{max}-p) \cdot \Delta z \quad (11)$$

where z represents a depth at which the center of the medium fragment is located.

Displacements of medium fragments corresponding to all data segments on the $n_1^{th}$ ultrasonic signal scanning line during the duration between the time $n_1 \cdot \Delta t$ and the time $(n_1+1) \cdot \Delta t$ may be acquired by repeating the above steps for each data segment on the $n_1^{th}$ ultrasonic signal scanning line, which constitute a sequence $d(z, t)|_{t=n_1 \cdot \Delta t, z=1 \cdot \Delta z, 2 \cdot \Delta z, 3 \cdot \Delta z, \ldots, (L-2m) \cdot \Delta z}$.

The strain in the viscoelastic medium on the $n_1^{th}$ ultrasonic signal scanning line may be calculated by differentiating the displacements in the depth direction according to the following formula:

$$\varepsilon(z, t)|_{t=n_1 \cdot \Delta t} = \frac{\partial d(z, t)}{\partial z} \quad (12)$$

A strain corresponding to each ultrasonic signal scanning line may be acquired by the above method.

(g) The propagation velocity of the elastic wave in the viscoelastic medium is calculated. Particularly, a phase of a shear wave at a central frequency $f_0$ of the elastic wave is calculated for each depth of the viscoelastic medium so as to calculate the propagation velocity of the elastic wave:

$$E(z, f) = FT(\varepsilon(z, t)) \quad (13)$$

$$\varphi(z) = \arg(E(z, f_0)) \quad (14)$$

$$V_s(z) = 2\pi f_0 \left(\frac{d\varphi(z)}{dz}\right)^{-1} \quad (15)$$

where FT is a Fourier transform, and φ(z) is a phase of E(z, f₀) at a frequency f₀.

(h) An elastic modulus of the viscoelastic medium is calculated. For a viscoelastic medium of a soft tissue of an animal or human body, there is a following relationship between the propagation velocity $V_s$ of the elastic wave and the elastic modulus E of the viscoelastic medium:

$$E = 3\rho V_s^2 \qquad (16)$$

where ρ is a density of the viscoelastic medium.

Therefore, an elastic modulus of the viscoelastic medium at a depth z may be calculated according to the following formula:

$$E(z) = 3\rho \left[ 2\pi f_0 \left( \frac{d\varphi(z)}{dz} \right)^{-1} \right]^2. \qquad (17)$$

Although explanatory embodiments have been shown and described, it would be appreciated by those skilled in the art that changes, alternatives, and modifications may be made in the embodiments without departing from spirit and principles of the disclosure. Such changes, alternatives, and modifications all fall into the scope of the claims and their equivalents.

What is claimed is:

1. A method for detecting an elasticity of a viscoelastic medium, comprising steps of:
   driving an ultrasonic transducer probe with a low-frequency vibration by a vibrator so as to produce an elastic wave in the viscoelastic medium;
   producing an ultrasonic wave by the ultrasonic transducer probe, and transmitting the ultrasonic wave to the viscoelastic medium;
   collecting an ultrasonic echo when the elastic wave is propagated in the viscoelastic medium and the ultrasonic transducer probe stops or almost stops vibrating;
   calculating an elastic parameter of the viscoelastic medium according to the collected ultrasonic echo, wherein
   a serial number $N_{select}$ of a collected ultrasonic echo satisfying:

$N_{select} \geq \text{ceiling}((T+\Delta T) \times F_{high})$, where ceiling(.) is a ceiling rounding function, $F_{high}$ is a pulse repetition frequency of transmitting an ultrasonic signal and is within a range from 100 Hz to 100000 Hz, T is the duration of the vibration, the ultrasonic transducer probe stops or almost stops vibrating after the vibration starts for a period of T+ΔT;
   when the elastic wave is propagated in the viscoelastic medium, the serial number $N_{select}$ of the collected ultrasonic echo satisfying:

$N_{select} \leq \text{ceiling}((D_1/V_{s1}+T) \times F_{high})$;

where, $D_1$ is a thickness of the viscoelastic medium, $V_{s1}$ is a lower limit of a propagation velocity of the elastic wave in the viscoelastic medium determined according to an estimated hardness range and an estimated density of the viscoelastic medium;
   when ΔT is less than $D_1/V_{s1}$ by combining above two formulae, $N_{select}$ satisfying:

$\text{ceiling}((T+\Delta T) \times F_{high}) \leq N_{select} \leq \text{ceiling}((D_1/V_{s1}+T) \times F_{high})$; and when ΔT is not less than $D_1/V_{s1}$ an elastic intermediate medium with a thickness of $D_2$ and a first hardness is added between the ultrasonic transducer probe and the viscoelastic medium so that $\Delta T < D_1/V_{s1} + D_2/V_{s2}$, where $V_{s2}$ is a propagation velocity of the elastic wave in the elastic intermediate medium, then the serial number $N_{select}$ of the collected ultrasonic echo satisfying:

$\text{ceiling}((T+\Delta T) \times F_{high}) \leq N_{select} \leq \text{ceiling}((D_2/V_{s2}+D_1/V_{s1}+T) \times F_{high})$.

2. The method according to claim 1, further comprising:
   detecting a pressure applied to the viscoelastic medium by the ultrasonic transducer probe;
   in response to the pressure applied to the viscoelastic medium satisfying a predetermined condition, driving the ultrasonic transducer probe with the low-frequency vibration by the vibrator.

3. The method according to claim 1, further comprising:
   detecting an average pressure and a pressure difference sensed on the viscoelastic medium by a pressure sensor array disposed on the ultrasonic transducer probe, and calculating a verticality parameter based on the average pressure and the pressure difference;
   in response to each of the average pressure and the verticality parameter satisfying a predetermined condition, driving the ultrasonic transducer probe with the low-frequency vibration by the vibrator.

4. The method according to claim 1, further comprising:
   acquiring with an ultrasonic imaging probe an ultrasonic image of the viscoelastic medium;
   determining an area to detect the elastic parameter of the viscoelastic medium according to the ultrasonic image.

5. The method according to claim 4, wherein,
   the ultrasonic image is a M-mode ultrasonograph, a two-dimensional ultrasonic image or three-dimensional ultrasonic image.

6. The method according to claim 1, wherein,
   a vibration frequency of the low-frequency vibration is between 0.5 Hz and 3000 Hz, and the duration of the low-frequency vibration is between 1/2f and 40/f;
   a frequency of the ultrasonic wave generated by the ultrasonic transducer probe is between 100 Hz and 10000 Hz.

7. A device for detecting an elasticity of a viscoelastic medium, comprising:
   a vibrator producing a low-frequency vibration;
   an ultrasonic transducer probe driven by the vibrator with the low-frequency vibration so as to produce an elastic wave in the viscoelastic medium; and
   a control apparatus connected with the ultrasonic transducer probe and the vibrator respectively, and configured to control the ultrasonic transducer probe to transmit an ultrasonic wave to the viscoelastic medium and to collect through the ultrasonic transducer probe an ultrasonic echo returned from the viscoelastic medium, and to calculate an elastic parameter of the viscoelastic medium according to the collected ultrasonic echo, wherein the ultrasonic echo is collected when the elastic wave is propagated in the viscoelastic medium and the ultrasonic transducer probe stops or almost stops vibrating,
   wherein
   a serial number $N_{select}$ of a collected ultrasonic echo satisfying:

$N_{select} \geq \text{ceiling}((T+\Delta T) \times F_{high})$, where ceiling(.) is a ceiling rounding function, $F_{high}$ is a pulse repetition frequency of transmitting an ultrasonic signal and is within a range from 100 Hz to 100000 Hz, T is the duration of the vibration, the ultrasonic transducer probe stops or almost stops vibrating after the vibration starts for a period of T+ΔT;

when the elastic wave is propagated in the viscoelastic medium, the serial number $N_{select}$ of the collected ultrasonic echo satisfying:

$N_{select} \leq \text{ceiling}((D_1/V_{s1}+T) \times F_{high})$;

where, $D_1$ is a thickness of the viscoelastic medium, $V_{s1}$ is a lower limit of a propagation velocity of the elastic wave in the viscoelastic medium determined according to an estimated hardness range and an estimated density of the viscoelastic medium;

when ΔT is less than $D_1/V_{s1}$ by combining above two formulae, $N_{select}$ satisfying:

$\text{ceiling}((T+\Delta T) \times F_{high}) \leq N_{select} \leq \text{ceiling}((D_1/V_{s1}+T) \times F_{high})$; and when ΔT is not less than $D_1/V_{s1}$ an elastic intermediate medium with a thickness of $D_2$ and a first hardness is added between the ultrasonic transducer probe and the viscoelastic medium so that $\Delta T < D_1/V_{s1}+D_2/V_{s2}$, where $V_{s2}$ is a propagation velocity of the elastic wave in the elastic intermediate medium, then the serial number $N_{select}$ of the collected ultrasonic echo satisfying:

$\text{ceiling}((T+\Delta T) \times F_{high}) \leq N_{select} \leq \text{ceiling}((D_2/V_{s2}+D_1/V_{s1}+T) \times F_{high})$.

8. The device according to claim 7, wherein the control apparatus comprises one of a computer, a microprocessor and a microcontroller, as well as an ultrasonic transmitting and receiving circuit connected with the one of the computer, the microprocessor and the microcontroller through a communication interface.

9. The device according to claim 7, wherein the control apparatus comprises a triggering key implemented by a hardware or a software for starting to detect the elastic parameter of the viscoelastic medium.

10. The device according to claim 7, further comprising a pressure sensor array mounted between and contacted with the ultrasonic transducer probe and the vibrator and configured to detect a pressure applied to the viscoelastic medium by the ultrasonic transducer probe, wherein the control apparatus further comprises a pressure signal collecting circuit connected with one of a computer, a microprocessor and a microcontroller through a communication interface.

11. The device according to claim 10, wherein the control apparatus is further configured to trigger the vibrator in response to the pressure applied to the viscoelastic medium satisfying a predetermined condition.

12. The device according to claim 10, wherein the control apparatus is further configured to detect an average pressure and a pressure difference on the viscoelastic medium according to the pressure detected by the pressure sensor array, to calculate a verticality parameter based on the average pressure and the pressure difference, and to trigger the vibrator in response to each of the average pressure and the verticality parameter satisfying a predetermined condition.

13. The device according to claim 7, further comprising an ultrasonic diagnostic equipment connected with the control apparatus for acquiring an ultrasonic image of the viscoelastic medium via an ultrasonic imaging probe thereof, wherein the control apparatus is further configured to determine an area to detect the elastic parameter of the viscoelastic medium according to the ultrasonic image.

14. The device according to claim 13, wherein,
the ultrasonic image is a M-mode ultrasonograph, a two-dimensional ultrasonic image or three-dimensional ultrasonic image.

15. The device according to claim 7, wherein,
a vibration frequency of the low-frequency vibration is between 0.5 Hz and 3000 Hz, and the duration of the low-frequency vibration is between 1/2f and 40/f;
a frequency of the ultrasonic wave generated by the ultrasonic transducer probe is between 100 Hz and 10000 Hz.

16. The device according to claim 7, further comprising a state indicating device for indicating a current working state of the device.

17. The device according to claim 7, further comprising a mechanical arm for supporting an ultrasonic probe consisting of the ultrasonic transducer probe and the vibrator.

* * * * *

UNITED STATES PATENT AND TRADEMARK OFFICE
CERTIFICATE OF CORRECTION

PATENT NO. : 10,426,432 B2
APPLICATION NO. : 15/279936
DATED : October 1, 2019
INVENTOR(S) : Shao et al.

It is certified that error appears in the above-identified patent and that said Letters Patent is hereby corrected as shown below:

On the Title Page

Item (73), the Assignee should read:
--(73) Assignee: WUXI HISKY MEDICAL TECHNOLOGIES CO., LTD., Wuxi (CN)--

Signed and Sealed this
Twenty-sixth Day of November, 2019

Andrei Iancu
*Director of the United States Patent and Trademark Office*